United States Patent [19]

Patterson

[11] Patent Number: 5,968,905
[45] Date of Patent: *Oct. 19, 1999

[54] STIMULATION OF NERVE GROWTH AND/OR VITALITY

[75] Inventor: Paul H. Patterson, Altadena, Calif.

[73] Assignee: California Institute of Technology, Pasadena, Calif.

[*] Notice: This patent is subject to a terminal disclaimer.

[21] Appl. No.: 08/904,876

[22] Filed: Aug. 1, 1997

Related U.S. Application Data

[63] Continuation of application No. 08/154,252, Nov. 18, 1993, Pat. No. 5,843,892, which is a continuation-in-part of application No. 07/451,635, Dec. 18, 1989, abandoned.

[51] Int. Cl.⁶ .................................................. A61K 38/18
[52] U.S. Cl. ........................................ 514/12; 424/85.1
[58] Field of Search .............................. 514/12; 424/85.1

[56] References Cited

U.S. PATENT DOCUMENTS

| | | | |
|---|---|---|---|
| 4,892,538 | 1/1990 | Aebischer et al. | 604/891.1 |
| 4,997,929 | 3/1991 | Collins et al. | 435/69.1 |
| 5,370,870 | 12/1994 | Wong et al. | 424/85.1 |

FOREIGN PATENT DOCUMENTS

91/14443  10/1991  WIPO.

OTHER PUBLICATIONS

Metcalf et al., "Fatal Syndrome in Mice Engrafted with Cells Producing High Levels of the Leukemia Inhibitory Factor," *Proc. Natl. Acad. Sci. USA*, 86(15):5948–5952 (1989).
Dunnett et al., "Acetylcholine–Rich Neuronal Grafts in the Forebrain of Rats: Effects of Environmental Enrichment, Neonatal Noradrenaline Depletion, Host Transplantation Site and Regional Source of Embryonic Donor Cells on Graft Size and Acetylcholinesterase–Positive Fibre Outgrowth," *Brain Research*, 378:357–373 (1986).
Norris, D.O., "Vertebrate Endocrinology" 2nd ed, Lea & Febiger:Philadelphia, pp. 238–249 (1985).
Estrov et al., "The Modulatory Hematopoietic Activities of Leukemia Inhibitory Factor," *Leukemia and Lymphoma*, 8:1–7 (1992).
Schehr, R.S., "Therapeutic Approaches to Alzheimer's Disease: An Informal Survey of Promising Drug Discovery Strategies," *Bio/Technology*, 12:140–144 (1994).
U.S. Congress, Office of Technology Assessment, "Neural Grafting: Repairing the Brain and Spinal Cord," OTA–BA–462, U.S. Government Printing Office:Washington, D.C., pp. 37–57 (1990).
Barres et al., "Multiple Extracellular Signals are Required for Long–Term Oligodendrocyte Survival," *Development*, 118:283–295 (1993).
Hilton et al., "Leukemia Inhibitory Factor: A Biological Perspective," *Journal of Cellular Biochemistry*, 46:21–26 (1991).
Yamamori et al., "The Cholinergic Neuronal Differentiation Factor from Heart Cells is Indentical to Leukemia Inhibitory Factor," *Science*, 246:1412–1416 (1989).
Cheema et al., "Leukemia Inhibitory Factor (LIF) Prevents the Death of Axotomized Sensory Neurons in Newborn Rat Dorsal Root Ganglion (DRG) In Vivo," *So. Neurosci. Abstract*, Abstract 27.2 18(1):47 (1992).
Richards et al., "Leukemia Inhibitory Factor Promotes the Neuronal Developmental of Spinal Cord Precursors From the Neural Tube," *Journal of Neuroscience Research*, 33:476–484 (1992).
Fukada, K., "Purification and Partial Characterization of a Cholinergic Neuronal Differentiation Factor," *Proc. Natl. Acad. Sci. USA*, 82:8795–8799 (1985).
Metcalf et al., Blood 76:50–56, Jul. 1990.

*Primary Examiner*—Robert A. Wax
*Assistant Examiner*—Gabriel E. Bugaisky
*Attorney, Agent, or Firm*—Flehr Hohbach Test Albritton & Herbert LLP

[57] ABSTRACT

The protein, cholinergic neuronal differentiation factor (CDF), also known as leukemia inhibitory factor (LIF), is described, together with the use of the polypeptide to stimulate neuron growth and survival in animals either by direct administration or by autotransplantation of adrenal medullary cells converted to the cholinergic phenotype.

4 Claims, 1 Drawing Sheet

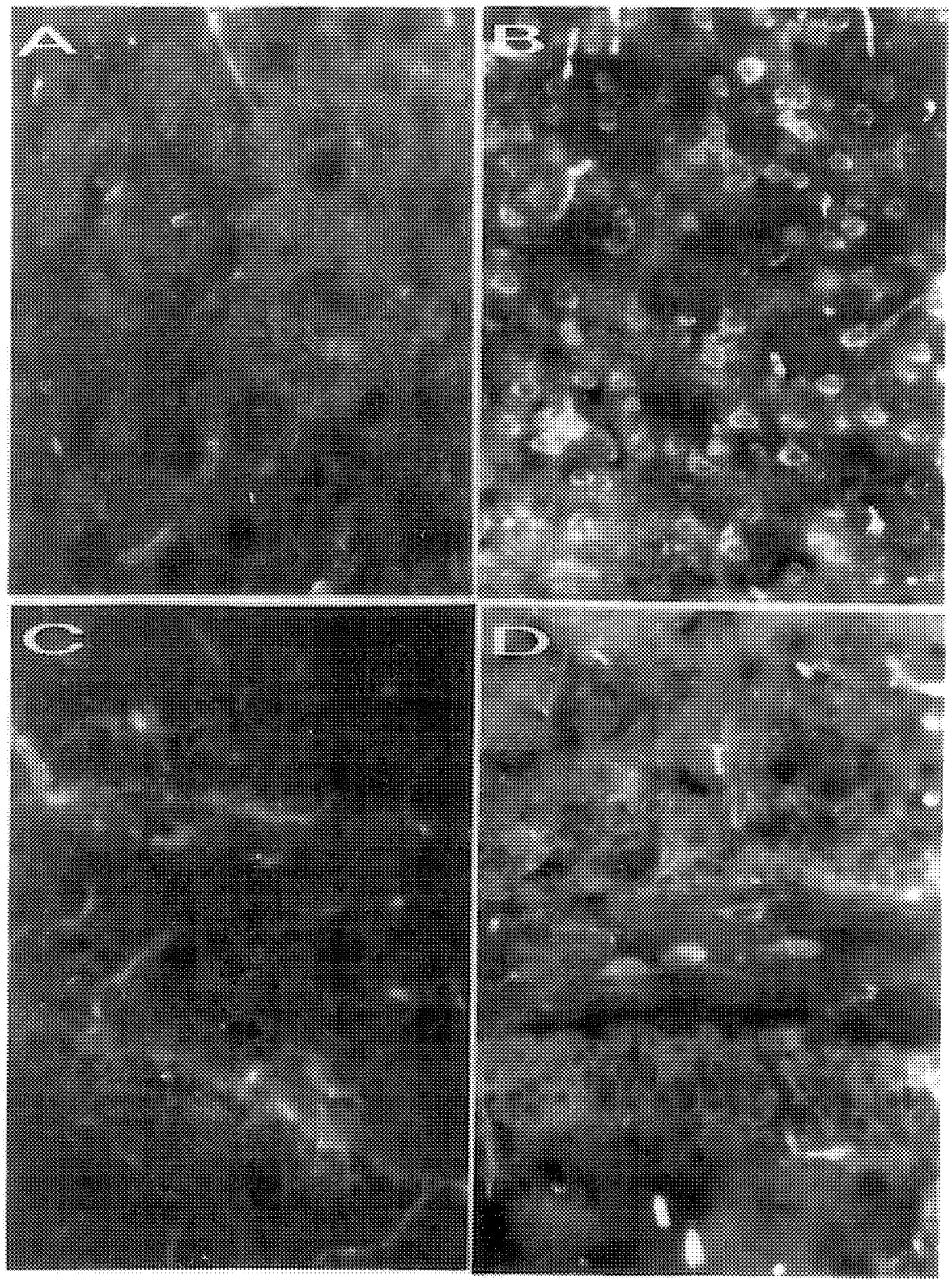

STIMULATION OF NERVE GROWTH AND/OR VITALITY

The following patent application is a continuation of Ser. No. 08/154,252, filed on Nov. 18, 1993, now U.S. Pat. No. 5,843,892 which is a continuation-in-part application of parent patent application, Ser. No. 07/451,635, filed on Dec. 18, 1989 now abandoned, the disclosures of which are expressly incorporated herein by reference.

BACKGROUND OF THE INVENTION

The present invention relates generally to the use of certain proteins of known amino acid sequence which stimulate neuron growth and differentiation, and the use of these proteins in animals to influence and mitigate disease states associated with neuron death.

A protein from rat heart that controls the development of neurons has been purified and characterized (Fukada, Proc. Natl. Acad. Sci. USA 82:8495, 1985). This protein, secreted into the medium of cultured heart cells, was found to induce cultured sympathetic neurons to synthesize acetylcholine and form cholinergic synapses, while suppressing catecholamine synthesis and noradenergic function. The amino acid sequence of this protein (CDF) was deduced and compared the sequence information to that available on the computer data base for all known proteins. It was discovered that the gene for the mouse version of the protein had been published (Gearing et al., EMBO J. 6:3995, 1987). The protein expressed by this gene, called LIF, for leukemia inhibitory factor, has been disclosed in European Patent Application Publication No. 0285448, published May 10, 1988, based an Application No. 88302962.1, the disclosure of which is expressly incorporated herein by reference.

The LIF protein will also be referred to herein as CDF, and is also known as human macrophage differentiation inducing factor (DIF).

The term "differentiation factor" is used because the protein controls phenotypic choices in these neurons without affecting their survival or growth.

CDF converts adrenal medullary cells to the production of acetylcholine (Doupe et al., J. Neuroscience 5:2119, 1985). This discovery implies that the protein may enhance acetylcholine synthesis in a variety of neurons, including those in the central nervous system when appropriately administered.

The importance of CDF is seen as three-fold. First, this protein can stimulate the growth of neurons. The ability to increase neuron vitality and to inhibit neuron death is of great importance in the treatment of diseases such as Alzheimer's and amyotrophic lateral sclerosis (ALS).

Secondly, it can be injected into the circulation or the central nervous system to alter the chemical balance of inhibitory versus excitatory nerves. The traditional method of doing this is to use pharmacological agents that block neurotransmitter receptors, or the enzymes that break down transmitters. CDF can be used to alter transmitters by changing the rate at which they are synthesized, by enhancing the rates of transcription of the messages for specific enzymes that synthesize transmitters. The transmitter balance in the case of sympathetic neurons is acetylcholine (which slows the heart beat) versus catecholamines (which speed the heart beat). In the central nervous system, acetylcholine is a transmitter of great interest in the pathology of Alzheimer's disease and ALS, the loss of this transmitter being one of the cardinal signs of these diseases.

Thirdly, the ability of CDF to convert adrenal medullary cells to acetylcholine production may be beneficial in providing a source of acetylcholine producing cells for autotransplantation to the brain as an alternative procedure for the treatment of Alzheimer's disease and other disease states associated with acetylcholine deficiency. There are a number of advantages in using a patient's own tissue for grafts. Autografts alleviate the need for immunosuppression, and the ethical, legal and availability problems associated with the use of fetal tissue are avoided. In addition, adrenal autografts with Parkinsonism have yielded a number of positive results. Thus, CDF is of potential medical benefit, and it is believed that the present invention represents a significant advance in the art.

SUMMARY OF THE INVENTION

Briefly, the present invention is comprised of the use of effective amounts of CDF/LIF to stimulate neuron growth and/or vitality and to use this protein to enhance the levels of acetylcholine in the nervous system.

It is an object of this invention to provide a new method of enhancing neuron growth and/or differentiation.

It is an object of this invention to provide a new method of stimulating the production of acetylcholine in animals in vivo.

It is a further object of this invention to provide a method of inducing the expression of acetylcholine and cholinergic function while suppressing catecholamine synthesis and noradenergic function in vivo.

It is an important object of this invention to stimulate the production of acetylcholine in animals to mitigate or treat disease states associated with acetylcholine deficiency.

A major object of this invention is to convert adrenal medullary cells to neurons that produce acetylcholine, before or after autotransplantation of the adrenal cells into the brain.

These and other objects and advantages of this invention will be apparent to those skilled in the art from the more detailed description which follows.

Example 1 discusses briefly the similarity between LIF obtained by recombinant procedures according to the above-identified European Patent Application Publication, and CDF known to be present in rat heart cell conditioned medium (CM) prepared according to P. H. Patterson and colleagues (Patterson, P. H. and Chun, L. L. Y (1974) Proc Natl. Acad Sci. 71, 3607–3610; Patterson, P. H. and Chun, L. L. Y (1977) Dev. Biol. 56, 263–280; Fukada, K., Proc. Natl. Acad Sci. USA 82:8795, 1985), in their amino acid sequence and in their ability to convert primary cultures of dissociated sympathetic neurons to the cholinergic phenotype.

Example 2 describes the conversion of adrenal medullary cells to cholinergic neurons, using the CDF.

Example 3 is intended to be illustrative of the practice of the present invention rather than to limit it. Example 3 describes an autotransplantation of the converted cells of Example 2 into a rat brain.

Example 4 is an in vivo young rat study in which a motor nerve was deliberately severed. Then, CDF was administered and rehabilitation of the neurons was observed.

Example 5 is a vivo adult mouse brain study in which the gene for CDF has been eliminated by homologous recombination.

The new results of this study indicate that the loss of this gene has multiple consequences that shed light on its normal function: (i) there are deleterious consequences for the brain in terms of neuronal survival and vitality; (ii) deletion of CDF yields a neuronal phenotype that is very reminiscent of the changes observed in cultured, cholinergic sympathetic neurons when CDF is removed—they revert to the noradenergic phenotype; (iii) lack of CDF yields an abnormal response to nerve injury, indicating that this agent is normally involved in the response to damage, and supporting the idea that this protein may prove efficacious in treating damage and disease in the central and peripheral nervous systems.

The isolation of the human version of the CDF/LIF and its use directly parallels the procedures described in these Examples.

The CDF/LIF protein from rats has this derived amino acid sequence:

MetLysValLeuAlaAlaGlyIleValProLeuLeuLeuLeuValLeu

HisTrpLysHlsGlyAlaGlySerProLeuProIleThrProValAsn

AlaThrCysAlaIleArgHisProCysHisGlyAsnLeuMetAsnGln

IleLysSerGlnLeuAlaGlnLeuAsnGlySerAlaAsnAlaLeuPhe

IleSerTyrTyrThrAlaGlnGLYGluProPheProAsnAsnValAsp

LysLeuCysAlaProAsnMetThrAspPheProProPheHisAlaAsn

GlyThrGluLysThrLysLeuValGluLeuTyrArgMetValAlaTyr

LeuGylAlaSerLeuThrAsnIleThrTrpAspGlnLysAanLeuAsn

ProThrAlaValSerLeuGlnIleLysLeuAsnAlaThrThrAspVal

MetArgGlyLeuLeuSerAsnValLeuCysArgLeuCysAsnLysTyr

HisValGlyHisValAspValProCysValProAspAsnSerSerLys

GluAlaPheGlnArgLysLysLeuGlyCysGlnLeuLeuGlyThrTyr

LysGlnValIleSerValValValGlnAlaPheTer.

DESCRIPTION OF PREFERRED EMBODIMENTS

The following examples are presented solely for purposes of Illustration.

EXAMPLE 1

That CDF is identical to LIF was published, Yamamori et al, Science 246., 1412–1416, (1989). In brief, it was demonstrated that the amino acid sequences of eight peptides from the purified rat CDF protein matched those deduced from the cDNA sequence of mouse LIF antiserum produced against one of these peptides was able to precipitate the cholinergic differentiation activity, showing that the protein purified and sequenced was indeed the correct factor. Moreover, recombinant mouse LIF was shown to have cholinergic differentiation activity when tested on cultured sympathetic neurons. The full sequence of CDF was then deduced after cloning the cDNA for this protein from rat heart cells (Yamamori et al, 1989).

EXAMPLE 2
EXPANSION OF ADRENAL CHRONAFFIN CELL NUMBERS AND CONVERSION TO THE CHOLINERGIC NEURONAL PHENOTYPE

Adrenal medullary chromaffin cells were grown in rat serum (from the same rat strain used for the chromaffin cells and for the graft recipients discussed in Example 3) by standard procedures (Doupe et al. (1985), J. Neurosci. 5:2119–2142). The synthetic corticosteroid dexamethasone was added if the cells are to be maintained in the chromaffin phenotype. For conversion into neurons, nerve growth factor (NGF) and heart cell (CM) containing CDF was added. The CM was serum-free, containing added epidermal growth factor and insulin, and it was concentrated and dialyzed before addition to the chromaffin cells. It was demonstrated that adrenal chromaffin cells, taken from neonatal or adult rats, could be converted to the cholinergic neuronal phenotype by this treatment.

In order to produce more adrenal-derived neurons from fewer donors, various conditions were tested to determine if chromaffin cells from adult rats could be stimulated to multiply in culture, and then be converted into neurons. Chromaffin cells from adult rats were plated into medium containing fibroblast growth factor (FGF) and dexamethasone. Many single cells and small clusters of cells were seen to expand in numbers, yielding large clusters of islands of cells. The increase cell number was quantified by counting chromaffin cells. Therefore, this paradigm is an effective way to increase the number of cells for grafting. After 9 days the medium is changed to one containing NGF and CM. During the weeks that followed, the chromaffin cells grew processes, enlarged, and became morphologically indistinguishable from sympathetic neurons.

EXAMPLE 3
GRAFTING OF CHOLINERGIC SYMPATHETIC NEURONS

For the initial grafting experiments, cholinergic sympathetic neurons were prepared from dissociated, neonatal ganglia. To enhance their Cholinergic differentiation, the neurons were grown in mixed cultures with ganglionic noneural cells and CM. The effect of the neuronal cells and/or can be duplicated by CDF. The neurons were cultured for 2–4 weeks before harvesting and grafting. Several methods of harvesting were tested; enzymatic dissociation from the dish produced low yields of healthy neurons, while mechanically rolling the cell layer up in a ball with a microscalpel appeared to damage the neurons less. This ball of cells, with intact processes was placed directly on the dorsal surface of the hippocampus of an adult rat brain that had been lesioned in the fimbria-fornix 2 weeks prior to grafting.

The survival and growth of the grafted neurons was assessed by several histological procedures. After 4–5 weeks, the general health and disposition of the graft was visualized by nissl and acetylcholinesterase staining. Noradenergic fibers were visualized by staining for tyrosine hydroxylase. These assays revealed that grafted sympathetic neurons do survive in the hippocampus. Immunohistochemistry reveals positive staining for both noradenergic fibers and acetylcholinesterase in the graft. It is likely that most of these neurons are dual-function, expressing both enzymes simultaneously. While the precise nature of the innervation of the hippocampus will require further study, it is most encouraging that the grafted neurons grow axons in the appropriate areas of the hippocampus.

The above illustrative examples are believed to establish that the CDF converts noradenergic cells to the cholinergic phenotype, and that such converted cells can be transplanted in vivo to the rat brain to enhance the number of cholinergic neurons. In addition, it is within the contemplation of this invention to administer CDF itself, either by direct injection into the brain tissue, or by systemic injection or infusion, to induce increased acetylcholine synthesis by the endogenous neurons of the otherwise intact (or desired) central nervous system. A study of this type is, in fact, presented in Example 4. The various surgical procedures for the harvesting of adrenal cells and for their autotransplantation into the brain, are, per se, already known to those skilled in the art.

EXAMPLE 4
EFFECTS OF CDF/LIF ON DEVELOPING MOTOR NEURONS IN VIVO

It is of interest to examine the role of CDF in the living animal. The recent observation that this protein can rescue dying motor neurons in culture (Martinou, J. C., Martinou, Paterson and Kato, AC Neuron 8:737–744 (1992)) raises the possibility that CDF could exert positive effects in vivo on neurons dying in diseases such as Alzheimer's.

The facial nerve is a purely cholinergic motor nerve. When this nerve was cut the first day after birth (P1) in rats, there was a significant decrease in the number of motor neurons that stain positively for choline acetyltransferase (ChAT), the enzyme that synthesizes acetylcholine, in the facial nerve nucleus. We quantitized this effect by comparing the ChAT+ neurons on the experimental (transected) side of the facial nucleus with those on the control side. In sham operated rats examined at P7, this ratio is 0.93. In contrast, the ratio in transected animals whose cut nerves were treated with gelfoam containing BSA is 0.06. That is, only 6% of the ChAT+ neurons are detectable on the operated side. In animals treated unilaterally with CDF/LIF, in contrast, our results indicated that more than four-fold more ChAT+ neurons are visualized (the experimental/control value is 0.26).

Total neuron counts were also carried out in the sections from these animals. These values allow us to express the data as the percent cells that stain ChAT+, and indicate that the ratio ChAT+/Nissl+ cells is also elevated by CDF/LIF treatment. The ratio in sham operated animals is 0.93, while the ratio in BSA-treated animals is 0.10 (operated side over control side). That is, only 10% of the cells on the transected side are ChAT+. In the animals whose nerves had been treated with CDF/LIF, in contrast, the ratio is 1.03.

These data support the hypothesis generated from the culture work that CDF/LIF is useful in enhancing motor neuron survival after nerve injury in vivo, by direct, local application.

EXAMPLE 5
CDF/LIF-DEFICIENT MICE DISPLAY DEFICIENCIES IN THE CENTRAL NERVOUS SYSTEM

To investigate the role of CDF/LIF in the intact central nervous system, the brains of adult mice in which the gene for the CDF/LIF protein was deleted by homologous recombination were examined. One question of interest here is whether these brains display evidence of a lack of cholinergic phenotype. These "knockout" mutant mice do not display obvious behavioral abnormalities nor do their brains exhibit gross morphological defects. To search for differences at the cellular level, we compared sections from wild type and knockout brains after staining for a variety of differentiation markers. There is an apparent loss of pyramidal neurons in the visual cortex but not in other cortical areas. The dentate gyrus shows not only shrunken cells but also a decrease in the thickness of the layer in the mutants. These changes are of particular interest because we have shown that these brain areas are the ones normally enriched in CDF and its receptor mRNA. This is also presumptive evidence that CDF maintains the survival and growth of neurons in the normal brain.

Another striking change in the mutant brains is a dramatic induction of the catecholaminergic enzyme, tyrosine hydroxylase, in the visual cortex and dentate gyrus. This observation is important because we showed that one of the cardinal effects of CDF in making cultured sympathetic remains cholinergic in the suppression of tyrosine hydroxylene (Patterson and Chun, 1974, 1977). Thus, the induction desuppression of tyrosine hydroxylase in the CDF knockout mice brains suggest this factor could be serving a similar role in the central nervous system.

BRIEF DESCRIPTION OF THE DRAWINGS

FIG. 1 in photos A and B are of the visual cortex. Photos C and D are of the hippocampus. Photos A and C are of the brains of normal mice. Photos B and D are of mice that have the gene for CDF/LIF removed.

Turning to the drawings in more detail, in FIG. 1, the brains of normal mice and nice that have had the gene for CDF/LIF deleted by homologous recombination are compared. Sections of the visual cortex (A,B) and hippocampus (C,D) are stained with an antibody to tyrosine hydroxylase, a catecholamine synthetic enzyme that is suppressed by CDF/LIF in cultured sympathetic neurons when they are induced to become cholinergic. It is readily apparent that tyrosine hydroxylase staining has been strikingly upregulated in the homozygous mutant mice lacking CDF/LIF (B,D) as compared to the wild type controls (A,C). This evidence supports the idea that CDF/LIF is a cholinergic differentiation factor in the brain as well as in the peripheral nervous system. Moreover, since the hippocampus is involved in learning and memory, and CDF/LIF mRNA, its receptor mRNA and now this phenotypic effect, are seen in the hippocampus, there is significant evidence that this factor may be important for proper development of this key function of the nervous system. This observation is important because it has previously been shown that one of the cardinal effects of CDF in making cultured sympathetic neurons cholinergic is the suppression of tyrosine hydroxylase. Thus, the induction or depression of tyrosine hydroxylase in the CDF knockout mice brains suggests that this factor could be serving a similar role in the central nervous system.

In addition, in collaborative work, it has been shown that the response to nerve injury is abnormal in the mutant mice. In the absence of CDF, nerve crush or transection (sympathetic or sciatic) in adult mice does not yield the same sets of neuropeptide induction that we observe in normal mice. These results demonstrate that CDF is required for the normal response to injury in peripheral nerves. Here too, the results of the knockout mice provide in vivo evidence of a role for CDF in neuronal vitality and differentiation (gene expression). These findings also support the hypothesis that CDF could be efficacious in the treatment of injured or diseased neural nerves.

These results indicate that CDF/LIF does indeed have a regulatory role in the brain in vivo.

These procedures are expected to provide an improvement in brain function in patients suffering from Alzheimer's disease and other related disease states.

Those skilled in the art can, by the exercise of ordinary skill, determine the effective amount of the polypeptide to administer directly or systemically. Likewise, the amount of polypeptide used to convert the adrenal cells and the amount of the converted cells implanted can also be determined by routine procedures.

Having fully described the invention, it is intended that it be limited only by the lawful scope of the appended claims.

What is claimed is:

1. A method for treating conditions requiring cholinergic nerve growth comprising administering cholinergic differentiation factor/leukemia inhibitory factor (CDF/LIF) to an animal, to adrenal medullary chromaffin cells, or to injured nerves, in an amount effective to stimulate cholinergic neuronal growth.

2. The method of claim 1 wherein the CDF/LIF is administered to adrenal medullary chromaffin cells to induce conversion to cholinergic neurons and growth of said cholinergic neurons.

3. The method of claim 1 wherein the required cholinergic nerve growth is in the brain.

4. A method for inducing cholinergic nerve growth comprising administering cholinergic differentiation factor/leukemia inhibitory factor (CDF/LIF) to an animal, to adrenal medullary chromaffin cells, or to injured nerves, in an amount effective to stimulate cholinergic nerve growth.

\* \* \* \* \*

UNITED STATES PATENT AND TRADEMARK OFFICE
CERTIFICATE OF CORRECTION

PATENT NO : 5,968,905
DATED : October 19, 1999
INVENTOR(S) : PATTERSON, PAUL H.

It is certified that error appears in the above-identified patent and that said Letters Patent is hereby corrected as shown below:

Title page,
AT [56] REFERENCES CITED

Column 2, line 18, delete "Indentical" and insert therefore --Identical--.

Column 2, at Assistant Examiner delete "Gabriel E. Bugaisky" and insert therefore --Gabriele E. Bugaisky--.

Column 1, immediately preceding BACKGROUND OF THE INVENTION, insert a new paragraph to read -- This invention was made Government support under Grant No. NS-20916 awarded by the National Institutes of Health. The Government has certain rights in this invention.--

Column 1, line 30, delete "based an" and insert therefore --based on--.

Column 3, line 18, delete "HisTrpLysH1s" and insert therefore --HisTrpLysHis--.

Column 3, line 46, delete "Science 246." and insert therefore --Science 246--.

UNITED STATES PATENT AND TRADEMARK OFFICE
CERTIFICATE OF CORRECTION

PATENT NO : 5,968,505
DATED : October 19, 1999
INVENTOR(S) : PATTERSON, PAUL H.

It is certified that error appears in the above-identified patent and that said Letters Patent is hereby corrected as shown below:

Column 3, line 57, delete "Yamamori et al," and insert therefore --Yamamori et al.,--.

Column 3, line 60, delete "CHRONAFFIN" and insert therefore --CHROMAFFIN--.

Column 5, line 1, delete "into the brain, are," and insert therefore --into the brain are,--.

Column 6, line 14, delete "nice" and insert therefore --mice--.

Signed and Sealed this

Sixteenth Day of January, 2001

*Attest:*

Q. TODD DICKINSON

*Attesting Officer*     *Commissioner of Patents and Trademarks*